US006264934B1

(12) United States Patent
Kantner et al.

(10) Patent No.: US 6,264,934 B1
(45) Date of Patent: Jul. 24, 2001

(54) LOW SURFACE TENSION COSMETIC COPOLYMERS

(75) Inventors: Steven S. Kantner, St. Paul; Richard A. Mallo, Woodbury; Ramesh C. Kumar, Maplewood, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/433,195

(22) Filed: Nov. 3, 1999

(51) Int. Cl.[7] .................. A61K 31/74; A61K 9/00; A61K 7/00; A61K 9/14; C08K 61/00
(52) U.S. Cl. .............. 424/78.03; 424/400; 424/401; 424/484; 424/487; 524/544; 514/772.3
(58) Field of Search ............ 424/78.03, 70, 424/401, 487, 484; 524/547, 544; 514/772.3

(56) References Cited

U.S. PATENT DOCUMENTS

| | | | |
|---|---|---|---|
| 3,786,116 | 1/1974 | Milkovich et al. | 260/885 |
| 3,842,059 | 10/1974 | Milkovich et al. | 260/93.5 |
| 4,972,037 | 11/1990 | Garbe et al. | 526/245 |
| 4,981,902 | * 1/1991 | Mitra et al. | . |
| 4,981,903 | * 1/1991 | Garbe et al. | . |
| 5,021,477 | * 6/1991 | Garbe et al. | . |
| 5,061,481 | 10/1991 | Suzuki et al. | 424/63 |
| 5,166,267 | 11/1992 | Cohn et al. | 525/177 |
| 5,209,924 | 5/1993 | Garbe et al. | 424/71 |
| 5,229,435 | 7/1993 | Sakai et al. | 523/105 |
| 5,480,634 | 1/1996 | Hayama et al. | 424/70.12 |
| 5,565,193 | 10/1996 | Midha et al. | 424/70.12 |
| 5,667,771 | 9/1997 | Carballada et al. | 424/70.12 |
| 5,753,216 | 5/1998 | Leitch et al. | 424/70.12 |

FOREIGN PATENT DOCUMENTS

| | | | |
|---|---|---|---|
| 0 391 273 | 10/1990 | (EP) | A61K/7/48 |
| 0 412 704 | 2/1991 | (EP) | A61K/7/06 |
| 0 412 770 | 2/1991 | (EP) | A61K/7/06 |
| 0 412 707 | 2/1994 | (EP) | A61K/7/06 |
| 2 086 914 | 5/1982 | (GB) | C08F/220/04 |
| WO 93/23446 | 11/1993 | (WO) | C08F/299/08 |

OTHER PUBLICATIONS

Yamashita et al., Polymer J. 14, 913 (1982).
ACS Polymer Preprints 25 (1), 245 (1984).
Makromol. Chem. 185, 9 (1984).

* cited by examiner

*Primary Examiner*—Thurman K. Page
*Assistant Examiner*—Blessing Fubara
(74) *Attorney, Agent, or Firm*—Yen Tong Florczak

(57) ABSTRACT

A vinylic copolymer comprising repeat units of A, B and C These copolymers have an acid content of 0.015 to 0.50 milliequivalents per gram of copolymer. Compositions that provide these copolymers in easily handled forms, and cosmetic compositions comprising the copolymer are also provided.

18 Claims, No Drawings

LOW SURFACE TENSION COSMETIC COPOLYMERS

FIELD OF THE INVENTION

The present invention relates to copolymers comprising silicone macromers. More specifically, the present invention relates to copolymers providing low surface tension that are useful in cosmetic compositions.

BACKGROUND OF THE INVENTION

Polysiloxane grafted acid containing (meth)acrylate copolymers for cosmetic use are the subject of several patent applications and patents, some of which are listed below. None disclose polymers with acidic monomer contents in the 0.05 to 3% range in their examples nor do they recognize the ability of such polymers to greatly reduce interfacial tension between a basic aqueous phase and a volatile methylsiloxane fluid phase in their specifications.

U.S. Pat. Nos. 4,981,903 and 5,021,477; J. E. Garbe and S. Mitra to 3M disclose a composition and hair compositions, respectively, comprising a copolymer of 0.01 to 50% silicone macromer, 0.1 to 99.9% acrylic or methacrylic monomer, and 0.1 to 99.9% highly polar monomer where said highly polar monomer has at least one hydroxyl, amino, or ionic group including quaternary ammonium, carboxylate salt, and sulfonic acid salt.

U.S. Pat. No. 4,981,902; S. Mitra and J. E. Garbe to 3M disclose non-pressure sensitive adhesive compositions comprising copolymers with a Tg of at least 20° C. having at least 30% methacrylic monomer, 3 to 30% polar monomer, and 3 to 30% silicone macromer.

U.S. Pat. Nos. 4,972,037 and 5,209,924; J. E. Garbe, S. S. Kantner, K. Kumar, and S. Mitra to 3M disclose polymer compositions of >0.1% fluorocarbon monomer, 0.01 to 30% polar monomer, 0.01 to 50% silicone macromer, and the balance acrylate or methacrylate monomer and their use in topical medical compositions.

U.S. Pat. No. 5,667,771; J. A. Carballada, L. A. Thaman, and M. P. Clariziato Procter & Gamble disclose a rinse-off hair care composition with a copolymer dissolved in a hydrophobic volatile solvent dispersed in a carrier. The copolymer has 45 to 85% hydrophobic vinyl monomer, 0 to 5% hydrophilic reinforcing monomer, and 25 to 50% silicone macromer. Examples disclose a 700,000 molecular weight 67/3/30 t-butyl acrylate/acrylic acid/11,000 molecular weight silicone macromer terpolymer.

U.S. Pat. No. 5,229,435; Y. Sakai and I. Saitoh to Shionogi & Co. and Nissin Chemical Industry disclose a skin-protecting composition comprising an uncrosslinked silicone-acrylic copolymer having 1 to 15% silicone macromer, 30 to 70% of an alkyl acrylate, 0 to 30% of an alkyl methacrylate, and 5 to 45% of a carboxyl containing monomer.

U.S. Pat. No. 5,061,481; K. Suzuki, T. Shimizu; M. Yamazoe, and T. Sugisaki to Kobayashi Kose disclose cosmetic compositions comprising an acryl-silicone graft copolymer having 5 to 66% silicone macromer with the balance being acrylate or methacrylate monomers with other compounds, including (meth)acrylic acid, optionally included.

U.S. Pat. Nos. 5,166,267 and 5,480,634; K. Hayama, K. Narazaki, and S. Kawaguchi to Mitsubishi Chemical disclose polymers for hair care products with 15 to 99.9% hydrophilic ethylenically unsaturated monomer, 0.1 to 85% silicone macromer, and 0 to 84.9% hydrophobic ethylenically unsaturated monomer.

SUMMARY OF THE INVENTION

The present invention provides a vinylic copolymer comprising repeat units of A, B and C. A is is derived from one or more ethylenically unsaturated monomers containing an acid and is present in an amount to provide an acid content of 0.015 to 0.50 milliequivalents per gram of copolymer. B is 47–97.95% of the copolymer, and is derived from one or more ethylenically unsaturated monomers optionally containing modifying groups in an amount that does not substantially interfere with the solubility of the copolymer in non-water miscible organic solvents. C is 2–50% of the copolymer, and is derived from one or more ethylenically unsaturated organosiloxane chains.

Compositions that provide these copolymers in easily handled forms, and cosmetic compositions comprising the copolymer are also provided.

DETAILED DESCRIPTION

Volatile methylsiloxane (VMS) fluids, including cyclomethicones (hexamethylcyclotrisiloxane or $D_3$, octamethylcyclotetrasiloxane or $D_4$, decamethylcyclopentasiloxane or $D_5$, and dodecamethylcyclohexasiloxane or $D_6$) and linear dimethicones (hexamethyl disiloxane and oligomers containing up to four dimethylsiloxane units), are widely used in cosmetic formulations. Due to their low heat of vaporization, they evaporate without producing a cooling or stinging effect, hence find use in antiperspirants and deodorants, lipsticks, and skin care lotions. They provide silky, non-oily emolliency and improved application, spreading, and rub-in to skin care, sun care, and color cosmetics. And they provide transient conditioning, easing wet combing and speeding drying while reducing tack in hair care applications.

Silicone (meth)acrylate copolymers also provide unique benefits in cosmetic formulations which compliment those of the VMS fluids in many cases. Structurally these are vinyl polymeric backbones grafted with polydimethylsiloxane moieties and hence combine the characteristics of acrylic resins and high molecular weight dimethicones. They are film forming agents which impart faster drying times; long lasting water repellency; a soft, smooth feel; and transfer resistance to cosmetic formulations.

It is desirable to incorporate both VMS fluids and silicone (meth)acrylate copolymers into cosmetic formulations. Unfortunately, many of the silicone (meth)acrylate copolymers disclosed in the prior art have high (10 to 25%) acidic monomer content which limits their solubility in VMS fluids, requiring the use of more polar phenyl or chloro substituted silicone fluids (see for example EP 412,704; R. E. Bolich, Jr. and P. M. Torgerson to Procter & Gamble and U.S. Pat. No. 5,753,216; S. H. Leitch, L. J. Bartz; and K. B. Fish to Procter & Gamble) which are more expensive, of lower volatility, and are diminished in the attractive properties of the VMS fluids due to their higher polarity. At somewhat lower (3 to 5%) acidic monomer content, the viscosity of the VMS/silicone (meth)acrylate solution can be unacceptably high at desirable loading levels, perhaps due to hydrogen bond or dipole-dipole interactions between the carboxylic acid moieties which the non-polar VMS solvent can't break up. Addition of a polar co-solvent, such as ethanol, can improve solubility and reduce viscosity of these polar monomer containing polymers. However, such polar co-solvents can eliminate the non-sting and lack of cooling advantages of the VMS fluid and will tend to preferentially partition into the aqueous phase when used in emulsions. Addition of polar solvents also tend to disrupt emulsion stability. An alternative is to increase the hydrophilicity of the vinyl polymeric backbone to the point where it is soluble in the polar phase with the silicone grafts remaining soluble in the non-polar phase as taught in U.S. Pat. No. 5,565,193; S. Midha, P. M. Torgerson, and C. Hall to Procter & Gamble. However this can lead to a viscous aqueous phase and will impart undesirable hydrophilicity that prolongs drying, imparts tack, and increases humidity and moisture sensitivity. Prior art silicone (meth)acrylates with only non-polar monomer content in the backbone have good solubility in VMS fluids and the relationship between polar monomer content and the polarity of the solvent required to dissolve it is understood (see for example EP 412,707; P. M. Torgerson, R. E. Bolich, Jr., and J. E. Garbe to Procter & Gamble and 3M).

Many cosmetics including foundation, skin lotion, mascara, and conditioners are supplied as water-in-oil or oil-in-water emulsions. With increasing concern about and regulation of volatile organic compounds (VOCs), the interest in including water in other formulations such as hair fixatives has also increased. When used in these emulsions, VMS fluids, which aren't miscible with water, are present in the non-polar phase. In order to obtain an emulsion that doesn't separate during storage addition of an ionic or nonionic surfactant or a thickener is required to impart stability. Thickener can detract from other properties, such as spreadability for a skin cream or the ability to spray a hairspray. The presence of a surfactant can also have an unintended, undesirable effect on the properties of the formulation, imparting hydrophilicity which lowers moisture resistance, serving as a plasticizer, potentially introducing irritancy, and promoting corrosion of the packaging.

It has been found that polymerization of low levels of acid co-monomer (0.015 to 0.50 milliequivalents of acid per gram of polymer) into silicone (meth)acrylate copolymers does not unduly affect its solubility in VMS fluids nor the resulting viscosity, but greatly reduces the interfacial tension between the VMS solution and aqueous solutions, particularly those with a basic pH. These copolymers thus behave as surface active agents, allowing for emulsification of the two phases with little or no additional surfactant required. This is surprising in light of the disclosure in WO 93/23446 (P. M. Torgerson and A. T. Balchunas to Procter & Gamble) which teaches that from about 20% to about 80% of hydrophilic monomer is required to provide dispersibility in aqueous formulations.

It has further been found that the copolymers of the present invention assist in holding water soluble dyes in color cosmetics on the skin. For example, a colored lotion cosmetic of the present invention exhibits superior staying power on the skin under a running water assault as compared to like lotions with different polymer or with no polymer.

The copolymer of the present invention is a vinylic copolymer comprising repeat units of A, B and C, wherein A provides an acid content of 0.015 to 0.50, preferably 0.02 to 0.40, milliequivalents per gram of copolymer, and is derived from an ethylenically unsaturated monomer containing an acid. Acid contents below 0.015 do not show significant reduction in surface tension. Acid contents above 0.50 can cause high viscosity or poor solubility for the copolymer in $D_5$ solution. B is 47–97.95% of the copolymer, and is derived from an ethylenically unsaturated monomer optionally containing modifying groups in an amount that does not substantially interfere with the solubility of the copolymer in volatile methyl silicones. C is 2–50% of the copolymer, and is derived from an ethylenically unsaturated organosiloxane chain.

Preferably, the unit A is derived from vinylic monomers such as acrylates, methacrylates, crotonates, itaconates and the like comprising acidic functionality.

The A units may preferably be derived from mono- or multifunctional carboxyl group containing molecules represented by the general formula:

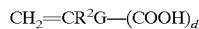

$$CH_2=CR^2G—(COOH)_d$$

where $R^2$=H, methyl, ethyl, carboxy or carboxymethyl, d is an integer of from 1 to 5 and G is a bond or a hydrocarbyl radical linking group containing from 1–12 carbon atoms of valence d+1 and optionally substituted with and/or interrupted with a substituted or unsubstituted heteroatom (such as O, S, N and P). Optionally, this unit may be provided in its salt form. The preferred monomers in this class are acrylic acid, methacrylic acid, itaconic acid, β-carboxyethyl acrylate and N-acryloyl glycine.

The unit B is derived from acrylate or methacrylate or other vinyl polymerizable starting monomers and optionally contains functionalities that modulate properties such as glass transition temperature, solubility in the carrier medium, hydrophilic-hydrophobic balance and the like.

Examples of unit B monomers include the (meth)acrylic acid esters of 1–18 carbon straight, branched or cyclic alcohols. More preferably, the B monomers include the (meth)acrylic acid esters of 2–12 carbon straight, branched or cyclic alcohols, and most preferably the 3–8 carbon straight, branched or cyclic alcohols. Other examples of B unit monomers include styrene, vinyl esters, vinyl chloride, vinylidene chloride, acryloyl monomers and the like.

Appropriate modifying groups that will not interfere with the solubility of the copolymer in $D_5$ include hydroxyl, ethers, amides and halides.

Examples of modifying groups that may interfere with the solubility of the copolymer in $D_5$ if present in too large a quantity include, for example, sulfates and amines. The amount of such modifying groups that can be tolerated in copolymers of the present invention depends on the specific identity and ratios of the A, B and C components. This amount can be readily predicted by a chemist of ordinary skill having benefit of the disclosure and intended objectives identified herein.

B may also optionally be derived from macromonomers such as those derived from styrene, α-methystyrene, vinyl toluene or methyl methacrylate. Preferably such macromonomers have a molecular weight of 500–100,000.

The unit C is preferably derived from an ethylenically unsaturated preformed organosiloxane chain. The molecular weight of this unit is generally above 500.

The unit C of the invention may be derived from a monomer having the general formula $X(Y)_n-Si(R)_{3-m}Z_m$ wherein X is a vinyl group copolymerizable with the A and B monomers;

Y is a divalent linking group (e.g., alkylene, arylene, alkarylene, and aralkylene of 1 to 30 carbon atoms) and incorporating heteroatoms e.g. O, N, S, P. Examples are ester, amide, urethane, urea groups.

n is zero or 1;

m is an integer of from 1 to 3;

R is hydrogen, lower alkyl (e.g., 1 to 4 carbon atoms, methyl, ethyl, or propyl), aryl (e.g., 6 to 20 carbon atoms, phenyl or substituted phenyl), or alkoxy (preferably lower alkoxy of 1 to 4 carbon atoms);

Z is a monovalent siloxane polymeric moiety having a number average molecular weight above about 500 and is essentially unreactive under copolymerization conditions;

The preferred C monomer may be further defined as having an X group which has the general formula

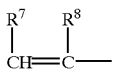

wherein $R^7$ is a hydrogen atom or a COOH group and $R^8$ is a hydrogen atom, a methyl group, or a $CH_2COOH$ group.

The Z group of the C monomer has the general formula

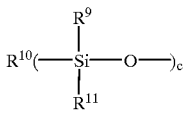

where $R^9$ and $R^{11}$ are independently lower alkyl, aryl, or fluoroalkyl, where lower alkyl and fluoroalkyl both refer to alkyl groups having from one to three carbon atoms and where aryl refers to phenyl or substituted phenyl (of up to 20 carbon atoms). $R^{10}$ may be alkyl (of 1 to 20 carbon atoms), alkoxy (of 1 to 20 carbon atoms), alkylamino (of 1 to 20 carbon atoms), aryl (of up to 20 carbon atoms), hydroxyl, or fluoroalkyl (of 1 to 20 carbon atoms), and e is an integer from about 5 to about 700. Preferably, the C monomer has a general formula selected from the group consisting of the following, where m is 1, 2, or 3, g is zero or 1, R" may be alkyl (of 1 to 10 carbon atoms) or hydrogen, f is an integer from 2 to 6, h is an integer from zero to 2, and X, R, and Z are as defined above:

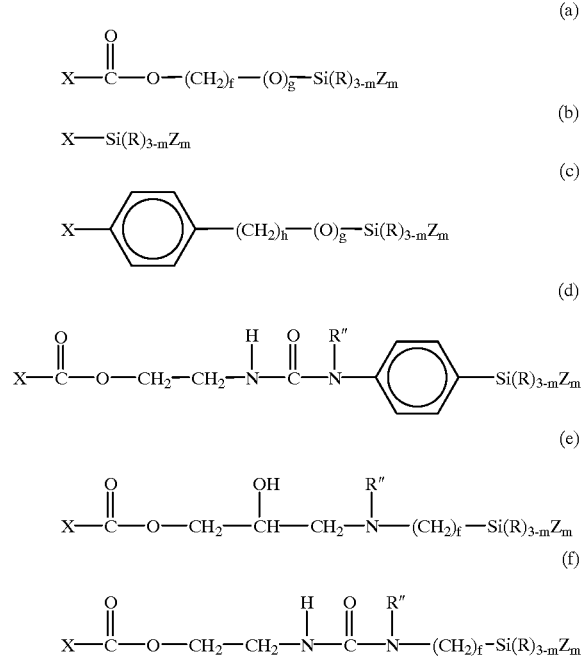

Particularly preferred polymers for use in the present invention have the composition wherein
the A group is derived from mono- or multifunctional carboxyl group-containing molecules represented by the general formula:

$CH_2=CR^2G$—$(COOH)_d$

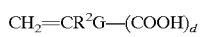

where $R^2$=H or methyl d=1, and
G is a bond or a hydrocarbyl radical linking group containing from 1–12 carbon atoms of valence d+1, or a salt thereof; the monomers of B are selected from the (meth)acrylic acid esters of 1–18 carbon straight, branched or cyclic alcohols and combinations thereof; and
the C group is derived from a monomer of the formula

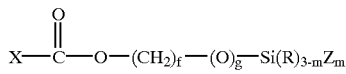

(b) $X$—$Si(R)_{3-m}Z_m$ wherein
X is a vinyl group copolymerizable with the A and B monomers;
m is an integer of from 1 to 3;
f is an integer from 2 to 6;
g is 0 or 1;
R is hydrogen or lower alkyl;
Z is a monovalent siloxane polymeric moiety having a number average molecular weight above about 500 and is essentially unreactive under copolymerization conditions.

Monomers used to provide the C unit of this invention are terminally functional polymers having a single functional group (vinyl, ethylenically unsaturated, acryloyl, or methacryloyl group) and are sometimes termed macromonomers or "macromers". Such monomers are known and may be prepared by the method disclosed by Milkovich et al., as described in U.S. Pat. Nos. 3,786,116 and 3,842,059. The preparation of polydimethylsiloxane macromonomer and subsequent copolymerization with vinyl monomer have been described in several papers by Y. Yamashita et al., [Polymer J. 14, 913 (1982); ACS Polymer Preprints 25 (1), 245 (1984); Makromol. Chem. 185, 9 (1984)].

This method of macromonomer preparation involves the anionic polymerization of hexamethylcyclotrisiloxane monomer ($D_3$) to form living polymer of controlled molecular weight, and termination is achieved via chlorosilane compounds containing a polymerizable vinyl group. Free radical copolymerization of the monofunctional siloxane macromonomer with vinyl monomer or monomers provides siloxane-grafted copolymer of well-defined structure, i.e., controlled length and number of grafted siloxane branches.

Suitable monomers for use in the above mentioned anionic polymerization are, in general, diorganocyclosiloxanes of the formula

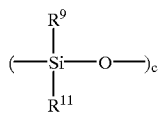

where $R^9$ and $R^{11}$ are as previously defined and where e is an integer of 3 to 7. Preferred are the cyclic siloxanes where e is 3 or 4 and $R^9$ and $R^{11}$ are both methyl, these cyclic siloxanes being hereafter designated $D_3$ and $D_4$, respectively. $D_3$, which is a strained ring structure, is especially preferred.

Initiators of the anionic polymerization are chosen such that monofunctional living polymer is produced. Suitable initiators include alkali metal hydrocarbons such as alkyl or aryl lithium, sodium, or potassium compounds containing up to 20 carbon atoms in the alkyl or aryl radical or more preferably up to 8 carbon atoms. Examples of such compounds are ethylsodium, propylsodium, phenylsodium, butylpotassium, octylpotassium, methyllithium, ethyllithium, n-butyllithium, sec-butyllithium, tert-butyllithium, phenyllithium, and 2-ethylhexyllithium. Lithium compounds are preferred as initiators. Also suitable as initiators are alkali metal alkoxides, hydroxides, and amides, as well as triorganosilanolates of the formula

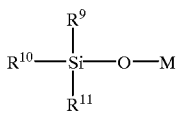

where M is alkali metal, tetraalkylammonium, or tetraalkylphosphonium cation and where $R^9$, $R^{10}$, and $R^{11}$ are as previously defined. The preferred triorganosilanolate initiator is lithium trimethylsilanolate (LTMS). In general, the preferred use of both strained cyclic monomer and lithium initiator reduces the likelihood of redistribution reactions and thereby provides siloxane macromonomer of narrow molecular weight distribution which is reasonably free of unwanted cyclic oligomers.

Molecular weight is determined by the initiator/cyclic monomer ratio, and thus the amount of initiator may vary from about 0.004 to about 0.4 mole of organometallic initiator per mole of monomer. Preferably, the amount will be from about 0.008 to about 0.04 mole of initiator per mole of monomer.

For the initiation of the anionic polymerization, an inert, preferably polar organic solvent can be utilized. Anionic polymerization propagation with lithium counterion requires either a strong polar solvent such as tetrahydrofuran, dimethyl sulfoxide, or hexamethylphosphorous triamide, or a mixture of such polar solvent with nonpolar aliphatic, cycloaliphatic, or aromatic hydrocarbon solvent such as hexane, heptane, octane, cyclohexane, or toluene. The polar solvent serves to "activate" the silanolate ion, making propagation possible.

Generally, the polymerization can be carried out at a temperature ranging from about −50° C. to about 100° C., preferably from about −20° C. to about 30° C. Anhydrous conditions and an inert atmosphere such as nitrogen, helium, or argon are required.

Termination of the anionic polymerization is, in general, achieved via direct reaction of the living polymeric anion with halogen-containing termination agents, e.g., functionalized chlorosilanes, to produce vinyl-terminated polymeric monomers. Such terminating agents may be represented by the general formula $X(Y)_nSi(R)_{3-m}Cl_m$, where m is 1, 2, or 3 and where X, Y, n, and R have been previously defined. A preferred terminating agent is methacryloxypropyldimethylchlorosilane. A second preferred terminating agent is methacryloxypropyldimethylfluorosilane, the preparation of which is described in U.S. Pat. No. 5,475,124. The termination reaction is carried out by adding a slight molar excess of the terminating agent (relative to the amount of initiator) to the living polymer at the polymerization temperature. According to the aforementioned papers by Y. Yamashita et al., the reaction mixture may be ultrasonically irradiated after addition of the terminating agent in order to enhance functionality of the macromonomer. Purification of the macromonomer can be effected by addition of methanol.

The copolymer used in this invention is conveniently prepared by copolymerizing the starting monomer units A, B and C by standard polymerization techniques.

The polymers of the present invention are preferably provided in non-water miscible organic solvents. For purposes of the present invention, a solvent is considered non-miscible if there is phase separation in a solution comprising one part solvent and nine parts water.

Preferred solvents include C4–C60 straight chain, branched, or cyclic alkyl and aromatic esters, including benzoates, octanoates, palmitates, alkyl acetates, and triglycerides; C4–C35 straight chain, branched, or cyclic alkyl and aromatic ethers, including propoxylated and ethoxylated alcohols; cyclic and linear volatile or non-volatile silicones, such as $D_5$; C4–C18 straight chain, branched, or cyclic alkyl alcohols; mineral oil; petroleum distillates and the like.

The polymer of the present invention may be applied via solutions, suspensions, gels, pastes, emulsions, (oil-in-water, water-in-oil or multiphase systems), as a dry powder, encapsulated or any other appropriate format.

The copolymers and composition comprising the copolymers as described herein are useful in various cosmetic compositions, such as hair styling agents, shampoos, dyes, conditioners, rinses, antidandruff preparations, shaving products, hand and body lotions, gels, creams, moisturizers, sunscreen compositions, sunless tanning compositions, cleansers, foundations, toners, astringents, fresheners, masks for the skin; polishes and strengtheners for the nails; underarm deodorants and antiperspirants, bath powders, talcs, bath oils, bubble baths, and makeup products for the eyes, cheeks, and lips such as foundation, mascara, lipstick, and other such colored cosmetic products; and colognes and perfumes.

Interfacial Tension Values

The following protocol is used to determine the Interfacial Tension Value of copolymers. Samples of copolymer are dissolved in $D_5$ at 5% solids. A Du Nouy ring is suspended below the air interface in a beaker containing either water (giving a "Water Solution Interfacial Tension Value.") or a 0.05 M NaOH solution (giving a "Basic Solution Interfacial Tension Value."). The $D_5$ solution of interest is carefully floated on top of the water and the interface allowed to equilibrate for 15 minutes at room temperature. The force required (in dynes per centimeter) to detach the ring from the water surface, moving it into the $D_5$ solution is measured using a Fisher Scientific Surface Tensiomat® 21 tensiometer. $D_5$ with no added polymer is also measured for comparison purposes. Two tests are conducted for each combination and the data averaged. Preferably, the Basic Solution Interfacial Tension Value is less than 10 dynes/cm, and more preferably less than 6 dynes/cm. Low interfacial tensions provide emulsions which require less energy to create, having smaller particle size and improved stability.

Viscosity of Standard Cosmetic Composition

The following protocol is used to determine the increase in viscosity measurement of a Standard Cosmetic Composition upon addition of 2% of a copolymer. The Standard Cosmetic Composition is selected to be representative of low viscosity formulations that one may encounter in the cosmetic industry, and is an indication of lack of undesirable interactions of the copolymer in all cosmetic formulations, even those of higher viscosity. Because the Standard Cosmetic Composition is relatively low in viscosity, it is sensitive to viscosity increasing effects of additives to cosmetic formulations and provides an ability to screen additives for difficulties in handling or manufacturing.

The Standard Cosmetic Composition without polymer has the following formula:

| PHASE | INGREDIENT | % W/W |
|-------|------------|-------|
| A | DEIONIZED WATER | 38.00 |
| A | CARBOPOL 940 (2% SOLN)[1] | 10.00 |
| A | PEMULEN TR-2 (2% SOLN)[2] | 10.00 |
| A | NA$_2$EDTA | 0.10 |
| A | PROPYLENE GLYCOL | 3.00 |
| B | OCTYL METHOXYCINNAMATE | 7.50 |
| B | OXYBENZONE | 4.00 |
| B | OCTYL SALICYLATE | 4.00 |
| B | FINSOLV TN[3] | 8.50 |
| B | LIPONATE GC[4] | 8.50 |
| B | FILM FORMER | 0.00 |
| B | EMERSOL 132 LILY[5] | 2.00 |
| B | MYRJ 52S[6] | 1.50 |
| B | CETEARYL ALCOHOL | 1.10 |
| C | TRIETHANOLAMINE 99% | 0.80 |
| D | GERMABEN II[7] | 1.00 |
|   | TOTAL | 100.00 |

[1]Carbomer from B. F. Goodrich
[2]Acrylates/C10–30 alkyl acrylate crosspolymer from B. F. Goodrich
[3]C12–15 alkyl benzoate from Finetex
[4]Caprylic/capric triglyceride from Lipo
[5]Stearic acid from Henkel
[6]PEG-40 stearate from ICI
[7]Methyl and propyl paraben and diazolidinyl urea in propylene glycol from Sutton Preparation: Heat phase A to 75° C. Heat phase B to 75° C. Add Phase B to Phase A. Add Phase C. Cool to 40° C. and add remaining phases The Standard Cosmetic Composition with polymer has the following formula:

| PHASE | INGREDIENT | % W/W |
|-------|------------|-------|
| A | DEIONIZED WATER | 38.00 |
| A | CARBOPOL 940 (2% SOLN)[1] | 10.00 |
| A | PEMULEN TR-2 (2% SOLN)[2] | 10.00 |
| A | NA$_2$EDTA | 0.10 |
| A | PROPYLENE GLYCOL | 3.00 |
| B | OCTYL METHOXYCINNAMATE | 7.50 |
| B | OXYBENZONE | 4.00 |
| B | OCTYL SALICYLATE | 4.00 |
| B | FINSOLV TN[3] | 4.15 |
| B | LIPONATE GC[4] | 4.15 |
| B | COPOLYMER IN D$_5$ (23%) | 8.70 |
| B | STEARIC ACID XXX | 2.00 |
| B | MYRJ 52S[5] | 1.50 |
| B | CETEARYL ALCOHOL | 1.10 |
| C | TRIETHANOLAMINE 99% | 0.80 |
| D | GERMABEN II[6] | 1.00 |
|   | TOTAL | 100.00 |

[1]Carbomer from B. F. Goodrich
[2]Acrylates/C10–30 alkyl acrylate crosspolymer from B. F. Goodrich
[3]C12–15 alkyl benzoate from Finetex
[4]Caprylic/capric triglyceride from Lipo
[5]PEG-40 stearate from ICI
[6]Methyl and propyl paraben and diazolidinyl urea in propylene glycol from Sutton Preparation: Heat phase A to 75° C. Heat phase B to 75° C. Add Phase B to Phase A. Add Phase C. Cool to 40° C. and add remaining phases.

This composition has 2% of a copolymer to be evaluated added as a 23% solids solution in D$_5$. When 100% solids polymer is used at 2% the absence of D$_5$ is balanced by increasing the loadings of Finsolve TN and Liponate CG equally to 7.5%. The steady state shear viscosities of both compositions are measured at a shear rate of 1 sec$^{-1}$ by using a Rheometrics Dynamic Analyzer RDA II with 25 mm diameter parallel plates at a gap of 1 mm at 23° C. The data was taken when the torque reached steady state and is expressed in Poise.

Preferably, the Standard Cosmetic Composition with copolymer has a steady state shear viscosity that is no more than 50% greater than the steady state shear viscosity of a Standard Cosmetic Composition without copolymer, more preferably no more than 25%, and most preferably no more than 10%. By minimizing the influence of copolymer addition on formulation viscosity, it allows the formulator to adjust copolymer loading independently from viscosity.

The following examples are given to illustrate, but not limit, the scope of this invention. Unless otherwise indicated, all parts and percentages are by weight, and all molecular weights are weight average molecular weight.

EXAMPLES

Polymer Example 1

Preparation of 69.9/0.1/30 Isobutyl Methacrylate/ acrylic Acid/10,000 Molecular Weight Monomethacryloxypropyl Terminated Polydimethyl Siloxane.

Into a one liter bottle charged 174.75 g isobutyl methacrylate (IBMA), 0.25 g acrylic acid (AA), 75 g 10,000 molecular weight mono-methacyloxypropyl terminated polydimethyl siloxane (10 K Si MAC), 250 g methylethyl ketone (MEK), and 0.5 g Vazo 64, azobis(isobutyronitrile) from DuPont. The resulting solution was purged of oxygen by bubbling nitrogen through it for 5 minutes at 5 liters per minute, the bottle sealed and tumbled in a constant temperature bath at 55° C. for 40 hours. After cooling, a solids test was performed finding 48.9% or 97.8% conversion. 50 g (containing 24 g of polymer) was placed in a round bottomed flask with 81.8 g decamethylcyclopentasiloxane (D$_5$). The resulting solution was concentrated on a rotary evaporator at 90° C. and 16.6 kilopascals vacuum to yield a slightly hazy homogeneous solution of 20% polymer in D$_5$ with a viscosity of 114 centipoise.

Polymer Example 2

Preparation of 69/1/30 IBMA/AA/10 K Si MAC

Following the procedure described in Example 1, a terpolymer with 172.5 g IBMA, 2.5 g AA, and 75 g 10 K SiMAC was prepared giving 49.4% solids (98.9% conversion). Dissolving a portion at 20% solids in D$_5$ gave a slightly hazy homogeneous solution with a viscosity of 186 centipoise after stripping the MEK.

Polymer Example 3

Preparation of 69.75/0.25/30 IBMA/AA/10 K Si MAC

Into a 100 mL bottle charged 14 g IBMA, 6 g 10 K Si MAC, 15 g MEK, 0.05 g Vazo 67 (azo bis (2-methyl butyronitrile) from Dupont), and 5.0 g of a solution of 199 mg AA in 19.7 g MEK. The resulting solution was purged of oxygen by bubbling nitrogen through it for 2 minutes at 5 liters per minute, the bottle sealed and tumbled in a constant temperature bath at 60° C. for 43 hours. 20 g (containing 10 g of polymer) was placed in a round bottomed flask with 40 g decamethylcyclopentasiloxane (D$_5$). The resulting solution was concentrated on a rotary evaporator at 90° C. and 16.6 kiloPascals vacuum to yield a slightly hazy homogeneous solution of 20% polymer in $D_5$ with a viscosity of 255 centipoise.

Polymer Example 4

Preparation of 68/2/30 IBMA/AA/10 K Si MAC

Following the procedure described in Example 3, a terpolymer with 13.6 g IBMA, 0.4 g AA, and 6 g 10K SiMAC was prepared in 20 g MEK initiating with 0.05 g Vazo 67 (azo bis (2-methyl butyronitrile) from Dupont). Dissolving a portion at 20% solids in $D_5$ gave a slightly hazy homogeneous solution with a viscosity of 328 centipoise after stripping the MEK.

Polymer Example 5

Preparation of 67/3/30 IBMA/AA/10 K Si MAC

Following the procedure described in Example 3, a terpolymer with 13.4 g IBMA, 0.6 g AA, and 6 g 10 K SiMAC was prepared in 20 g MEK initiating with 0.05 g Vazo 67 (azo bis (2-methyl butyronitrile) from Dupont). Dissolving a portion at 20% solids in $D_5$ gave a hazy homogeneous solution with a viscosity of 122 centipoise after stripping the MEK.

Comparative Polymer Example 1

Preparation of 70/30 IBMA/10K Si MAC

Into a one liter bottle charged 112 g IBMA, 48 g 10K Si MAC, 240 g ethyl acetate (EtOAc), and 0.8 g Vazo 64, azobis(isobutyronitrile) from DuPont. After purging and reacting as described in Example 1, a 39.1% solids (97.7% conversion) solution was obtained. Dissolving a portion at 20% solids in $D_5$ gave a clear homogeneous solution with a viscosity of 156 centipoise after stripping the EtOAc.

Comparative Polymer Example 2

Preparation of 67/3/30 t-Butyl acrylate/AA/10 K Si MAC.

Following the procedure for Copolymer 4 disclosed in U.S. Pat. No. 5,667,771; 67 g t-butyl acrylate (t-BA), 3 g AA, 30 g 10K Si MAC, 0.58 g Vazo 64 (azobis (isobutyronitrile) from DuPont), and 400 g EtOAc were charged into a one liter bottle then purged, sealed, and reacted as described in Example 1 to yield a 19.6% solids (98% conversion) solution. Dissolving a portion at 20% solids in $D_5$ gave a clear homogeneous gel with a viscosity of 1560 after stripping the EtOAc.

Comparative Polymer Example 3

Preparation of 80/10/10 IBMA/methacrylic acid/15 K Si MAC

Following the procedure of Example 7 in U.S. Pat. No. 4,981,902: 24 g 15K Si MAC (substituted for 20K used in '902), 12 g methacrylic acid (MAA), 84 g IBMA, 0.6 g benzoyl peroxide, and 240 g EtOAc were charged into a one liter bottle then purged, sealed, and reacted as described in Example 1 to yield a 33.7% solids (101% conversion) solution. Attempts to dissolve a portion at 20% solids in $D_5$ resulted in precipitation of a white solid.

Comparative Polymer Example 4

Preparation of 70/10/10 n-Butyl methacrylate/AA/ 15 K Si MAC

Following the procedure of Example 3 in U.S. Pat. No. 4,981,902: 28 g 15K Si MAC (substituted for 20K used in '902), 14 g AA, 98 g n-butyl methacrylate (BMA), 0.7 g benzoyl peroxide, and 326 g EtOAc were charged into a one liter bottle then purged, sealed, and reacted as described in Example 1 to yield a 27.9% solids (93% conversion) solution. Attempts to dissolve a portion at 20% solids in $D_5$ resulted in precipitation of a white solid.

Comparative Polymer Example 5

Preparation of 69.95/0.05/30 IBMA/AA/10K Si MAC.

Following the procedure described in Example 3, a terpolymer of 14 g IBMA, 6 g 10K Si MAC, and 10 milligram AA (adding 1.0 g of a solution of 199 mg AA in 19.7 g MEK) was prepared in 19 g additional MEK with 0.05 g Vazo 67 (azo bis (2-methyl butyronitrile) from Dupont). Dissolving a portion at 20% solids in $D_5$ gave a slightly hazy homogeneous solution with a viscosity of 123 centipoise after stripping the MEK.

Comparative Polymer Example 6

Preparation of 66/4/30 IBMA/AA/10K Si MAC

Following the procedure described in Example 3, a terpolymer of 13.2 g IBMA, 0.8 g AA, and 6 g 10K Si MAC was prepared in 20 g MEK with 0.05 g Vazo 67 (azo bis (2-methyl butyronitrile) from Dupont). Dissolving a portion at 20% solids in $D_5$ gave a cloudy solution with a viscosity of 134 centipoise after stripping the MEK.

Comparative Polymer Example 7

Preparation of 65/5/30 IBMA/AA/10K Si MAC

Following the procedure described in Example 3, a terpolymer of 13 g IBMA, 1 g AA, and 6 g 10K Si MAC was prepared in 20 g MEK with 0.05 g Vazo 67 (azo bis (2-methyl butyronitrilc) from Dupont). Dissolving a portion at 20% solids in $D_5$ gave a cloudy solution with a viscosity of 154 centipoise after stripping the MEK.

Comparative Polymer Example 8

Polysilicone-7

Polysilicone 7 is an IBMA/2-(N-methylheptadecafluorooctylsulfonamido)ethyl acrylate/Si MAC copolymer commercially available from 3M under the trade name Silicones Plus SA-70-5. It is a 23% solids solution of polymer in $D_5$ and was diluted to 20% with additional $D_5$ to yield a slightly hazy homogeneous solution with a viscosity of 89 centipoise.

Comparative Polymer Example 9

Acrylates/Dimethicone Copolymer

Acrylates/Dimethicone Copolymer is a copolymer of dimethicone and one or more monomers of AA, methacrylic acid, or one of their simple esters available from Shin Etsu under the trade name KP545. It is a 30% solids solution of polymer in $D_5$ and was diluted to 20% with additional $D_5$ to yield a clear homogeneous solution with a viscosity of 23 centipoise.

Comparative Polymer Example 10

PVP/Eicosene Copolymer. PVP/eicosene copolymer is a 100% solids copolymer of N-vinyl pyrrolidone and eicosene available from ISP under the tradename Ganex V220. It was used as received in the Standard Cosmetic Composition Interfacial Tension Measurements Samples of Examples 1 and 2 and Comparative Example 1 in $D_5$ were diluted to 5% solids with additional $D_5$. A Du Nouy ring was suspended below the air interface in a beaker containing either water or a 0.05 M NaOH solution. The $D_5$ solution of interest was carefully floated on top of the water and the interface allowed to equilibrate for 15 minutes at room temperature. The force required (in dynes/centimeter) to detach the ring from the water surface, moving it into the $D_5$ solution was measured using a Fisher Scientific Surface Tensiomat® 21 tensiometer. $D_5$ with no added polymer was also measured. Two tests were conducted for each combination and the data averaged. Results are shown in Table 1.

Determination of Acid Content

Portions of the polymer solutions prepared in Examples 1–5 and Comparative Examples 1 and 5–9 were poured into aluminum weighing tins and placed briefly on a hot plate at medium heat to drive off most of the solvent. The resulting polymers were dried further in a vacuum oven at 60° C. and 1.4 kiloPascals vacuum for 20 hours. A one gram sample of each polymer was analytically weighed into a 100 mL jar and 50 mL of tetrahydrofuran was added. After shaking to dissolve, 2 g of deionized water and 0.2 g of a 0.5% phenolphthalein in tetrahydrofuran was charged. The resulting solution was titrated to a pink endpoint with 0.100 molar aqueous sodium hydroxide. A blank containing no polymer was also run and the volume of sodium hydroxide required to reach the endpoint was subtracted from the volumes required for the polymers prior to calculating the acid content. Titrations were done in duplicate and averaged. Results are shown in Table 1.

TABLE 1

| Example | Water Solution Interfacial Tension (dynes/cm) | Basic Solution Interfacial Tension (dynes/cm) | Theoretical Acid Content (mequiv/g) | Measured Acid Content (mequiv/g) |
|---|---|---|---|---|
| Neat $D_5$ | 26.4 | 24.8 | | |
| Comp 1 | 20.5 | 19.6 | 0 | 0.006 |
| Comp 5 | 19.8 | 16.7 | 0.007 | 0.009 |
| 1 | 17.1 | 8.6 | 0.014 | 0.022 |
| 3 | 18 | 9.2 | 0.035 | 0.034 |
| 2 | 14.8 | 4 | 0.139 | 0.135 |
| 4 | 18 | 5.6 | 0.278 | 0.266 |
| 5 | 19.7 | 5.8 | 0.416 | 0.369 |
| Comp 6 | 19 | 10.2 | 0.555 | 0.519 |
| Comp 7 | 20.7 | 10.5 | 0.694 | 0.589 |
| Comp 8 | 17.7 | 8.1 | | 0.022 |
| Comp 9 | 14.4 | 12.8 | | 0.011 |

Viscosity of Standard Cosmetic Composition

The Standard Cosmetic Composition described previously was prepared with no film former, a 23% solids solution of the Polymer Example 1 terpolymer in $D_5$, a 23% solids solution of the Comparative Polymer Example 8 terpolymer in $D_5$, and the 100% solids copolymer of Comparative Polymer Example 10. After allowing these compositions to dwell at room temperature for 2 days, the steady state shear viscosity was measured using the parallel plate method detailed above. Results are shown in Table 2.

TABLE 2

| Polymer | Steady State Shear Viscosity (Poise) | Percentage Greater Than Composition Without Polymer |
|---|---|---|
| None | 323 | 0% |
| Example 1 | 311 | −4% |
| Comparative Ex. 8 | 408 | +26% |

TABLE 2-continued

| Polymer | Steady State Shear Viscosity (Poise) | Percentage Greater Than Composition Without Polymer |
|---|---|---|
| Comparative Ex. 10 | 813 | +152% |

Composition Examples

All composition examples were prepared using the terpolymer prepared in Polymer Example 1.

Composition Example 1

Lipstick:

Melt (<100° C.) and mix the follow ingredients then pour into suitable mold. Allow to cool.

| | |
|---|---|
| bees wax | 3.8% |
| carnauba wax | 9.4% |
| Cyclopentamethicone ($D_5$) | 30.4% |
| Isopropyl myristate | 9.3% |
| methyl paraben | 0.1% |
| Ozokerite wax | 9.4% |
| Paraffin | 5.8% |
| Pigment | 8.9% |
| propyl paraben | 0.1% |
| sun flower oil | 7.7% |
| 23% polymer in $D_5$ | 15.0% |
| Total | 100.0% |

Composition Example 2

Heavy Hand Cream (water in oil emulsion):

Mix and heat to 75° C. phase A and B separately. With homogenization slowly add phase B to phase A. After emulsion is formed cool to 40° C. using gentle mixing.

| | |
|---|---|
| Phase A | |
| Cyclotetramethicone (D4) | 12.9% |
| Petrolatum | 15.1% |
| Octadecanol | 3.0% |
| Abil EM90[1] | 2.0% |
| 23% polymer in cyclopentamethicone | 27.0% |
| Phase B | |
| Water | 37.8% |
| Propylene glycol | 2.0% |
| methyl paraben | 0.3% |
| Total | 100.0% |

[1]Cetyl dimethicone copolyol from Goldschmidt

Composition Example 3

Hand Lotion (oil in water emulsion):

Mix and heat to 75° C. phase A and B separately. With homogenization slowly add phase B to phase A. After emulsion is formed cool to 40° C. using gentle mixing.

| | |
|---|---|
| Phase A | |
| Water | 66.0% |
| triethanol amine | 0.7% |
| 1,3 butylene glycol | 4.9% |
| Tween 80[1] | 2.0% |

-continued

| Phase B | |
|---|---|
| Cyclotetramethicone | 5.9% |
| Arlacel C[2] | 1.0% |
| stearic acid | 2.6% |
| Octadecanol | 1.7% |
| 23% polymer in cyclopentamethicone | 15.2% |

[1]Polysorbate 80 from ICI
[2]Sorbitan sequioleate from ICI

Composition Example 4

Light Fast Drying Hand Lotion with smooth silky feel (water in oil emulsion):

Mix and heat to 75° C. phase A and B separately. With homogenization slowly add phase B to phase A. After emulsion is formed cool to 40° C. using gentle mixing.

| Phase A | |
|---|---|
| Cyclotetramethicone | 13.1% |
| mineral oil | 9.0% |
| 23% polymer in cyclopentamethicone | 6.0% |
| Abil EM90[1] | 2.0% |
| Phase B | |
| Water | 68.4% |
| propylene glycol | 1.4% |
| methyl paraben | 0.1% |

[1]Cetyl dimethicone copolyol from Goldschmidt

Composition Example 5

Liquid Color Make Up using water soluble dye:

Mix and heat to 75C. phase A and B separately. With homogenization slowly add phase B to phase A. After emulsion is formed cool to 40C using gentle mixing.

| Phase A | |
|---|---|
| Cyclotetramethicone | 5.0% |
| mineral oil | 10.5% |
| 23% polymer in cyclopentamethicone | 17.7% |
| Abil EM90[1] | 2.0% |
| Phase B | |
| Water | 63.3% |
| propylene glycol | 1.3% |
| methyl paraben | 0.1% |
| water soluble dye | 0.1% |

[1]Cetyl dimethicone copolyol from Goldschmidt

Composition Example 6

Liquid Color Make Up using dye lake:

Mix and heat to 75° C. phase A and B separately. With homogenization slowly add phase B to phase A. After emulsion is formed cool to 40° C. using gentle mixing.

| Phase A | |
|---|---|
| Cyclotetramethicone | 5.0% |
| mineral oil | 10.5% |
| 23% polymer in cyclopentamethicone | 17.7% |

-continued

| | |
|---|---|
| Abil EM90[1] | 2.0% |
| Phase B | |
| Water | 62.8% |
| propylene glycol | 1.3% |
| methyl paraben | 0.1% |
| water soluble dye lake particles | 0.6% |

[1]Cetyl dimethicone copolyol from Goldschmidt

Liquid Foundation:

Mix and heat to 750° C. phase A and B separately. With homogenization slowly add phase B to phase A. After emulsion is formed cool to 40° C. using gentle mixing.

| Phase A | |
|---|---|
| Water | 49.0% |
| propylene glycol | 9.9% |
| Monosil PLN (phosolipid)[1] | 3.0% |
| Lauriciden[2] | 2.0% |
| Triethanolamine | 1.0% |
| Talc | 2.1% |
| magnesium sulfate | 1.0% |
| TiO$_2$ | 1.0% |
| red iron oxide | 1.0% |
| methyl paraben | 0.1% |
| Phase B | |
| Finsolv TN[3] | 16.7% |
| stearic acid | 2.0% |
| Brij 30[4] | 0.1% |
| 100 cst dimethicone | 1.0% |
| 23% polymer in cyclopentamethicone | 10.0% |
| Tea tree oil | 0.2% |

[1]Polysiloxy linoleyl pyrrolidone phospholipid from Mona Industries
[2]Glyceryl laurate from Lauricidin
[3]C12–15 alkyl benzoate for Finetex
[4]Laureth-4 from ICI

Composition Example 8

Jojoba Oil Hand Lotion with smooth silky feel (water in oil emulsion):

Mix and heat to 75° C. phase A and B separately. With homogenization slowly add phase B to phase A. After emulsion is formed cool to 40° C. using gentle mixing.

| Phase A | |
|---|---|
| Cyclotetramethicone | 13.1 % |
| Jojoba Oil | 9.0% |
| 23% polymer in cyclopentamethicone | 6.0% |
| Abil EM90[1] | 2.0% |
| Phase B | |
| Water | 68.4% |
| propylene glycol | 1.4% |
| methyl paraben | 0.1% |

[1]Cetyl dimethicone copolyol from Goldschmidt

Composition Example 9

SPF 15 Sunscreen:

Mix and heat to 75° C. phase A and B separately. With homogenization slowly add phase B to phase A. Add phase C. After emulsion is formed cool to 40° C. using gentle mixing. Add phase D and mix.

| Phase A | |
|---|---|
| Water | 38.0% |
| Carbopol 940[1] | 10.0% |
| Pemulen TR-2[2] | 10.0% |
| Sodium EDTA | 0.1% |
| Propylene Glycol | 3.0% |
| Phase B | |
| Octyl Methoxycinnamate | 7.5% |
| Oxybenzone | 4.0% |
| Octyl Salicylate | 4.0% |
| Finsolv TN[3] | 4.2% |
| Liponate GC[4] | 4.2% |
| 23% polymer in cyclopentamethicone | 8.7% |
| stearic acid | 2.0% |
| MYRJ 52S[5] | 1.5% |
| cetearyl alcohol | 1.1% |
| Phase C | |
| Triethanolamine | 0.8% |
| Phase D | |
| Germaben II[6] | 1.0% |

[1]Carbomer from B. F. Goodrich
[2]Acrylates/C10–30 alkyl acrylate crosspolymer from B. F. Goodrich
[3]C12–15 alkyl benzoate from Finetex
[4]Caprylic/capric triglyceride from Lipo
[5]PEG-40 stearate from ICI
[6]Methyl and propyl paraben and diazolidinyl urea in propylene glycol from Sutto Composition Example 10
Eye shadow and blusher/rouge:

| | |
|---|---|
| carnauba wax | 2.8% |
| isopropyl miristate | 6.8% |
| ozokerite wax | 6.9% |
| Parafin | 4.2% |
| Pigment | 13.1% |
| sun flower oil | 4.8% |
| bees wax | 2.8% |
| Cyclopentamethicone | 32.1% |
| propyl parabin | 0.1% |
| methyl parabin | 0.1% |
| Phenylmethicone | 11.3% |
| 23% polymer in cyclopentamethicone | 15.0% |

Melt and mix the above ingredients and pour into delivery package.

Composition Example 11
Nail Polish:
Mix the following ingredients at room temperature in a ball mill overnight.

| | |
|---|---|
| 100% solids polymer | 16% |
| Red iron oxide | 2% |
| Mica UF | 2% |
| Butyl acetate | 48% |
| Ethyl acetate | 24% |
| Isopropanol | 8% |
| Total | 100% |

Composition Example 12
Styling Shampoo:
Disperse the first ingredient in the second, charge the next two and mix well, then charge the final ingredient and mix.

| | |
|---|---|
| Jaguar HP60[1] | 1.1% |
| Water | 34.1% |
| Incronam 30[2] | 13.2% |
| Standapol A[3] | 39.7% |
| 23% polymer in D$_5$ | 11.9% |
| Total | 100% |

[1]Hydroxy propyl guar from Rhone Poulenc
[2]Cocamidopropyl betaine from Croda
[3]Ammonium lauryl sulfate from Henkel Composition Example 13
Mascara:
Mix and heat to 80° C. phase A and B separately. With homogenization slowly add phase B to phase A. After emulsion is formed cool to 40° C. using gentle mixing.

| Phase A | |
|---|---|
| Water | 38.5% |
| Triethanol amine | 2.0% |
| PVP K30 | 2.0% |
| Natrosol 250 LR[1] | 1.0% |
| Propylene glycol | 5.0% |
| Cosmetic black | 10.0% |
| Phase B | |
| Glyceryl monostearate | 4.0% |
| White beeswax | 8.0% |
| Stearic acid | 4.5% |
| Carnuba wax | 5.0% |
| 23% polymer in D$_5$ | 20.0% |
| Total | |

[1]Hydroxyethyl cellulose from Aqualon

What is claimed is:
1. A vinylic copolymer comprising repeat units of A, B and C, wherein
   A is 0.06% to less than 2% of the copolymer, and is derived from one or more ethylenically unsaturated monomers containing an acid;
   B is 47–97.95% of the copolymer, and is derived from one or more ethylenically unsaturated monomers optionally containing modifying groups in an amount that does not substantially interfere with the solubility of the copolymer in non-water miscible organic solvents; and
   C is 2–50% of the copolymer, and is derived from one or more ethylenically unsaturated organosiloxane chains.
2. The copolymer of claim 1, wherein A is selected from mono- or multifunctional carboxyl group containing molecules represented by the general formula:

$$CH_2=CR^2G-(COOH)_d$$

where $R^2$=H, methyl, ethyl, carboxy or carboxymethyl, d is an integer of from 1 to 5 and G is a bond or a hydrocarbyl radical linking group containing from 1–12 carbon atoms of valence d+1 and optionally substituted with and/or interrupted with a substituted or unsubstituted heteroatom (such as O, S, N and P).
3. The copolymer of claim 1, wherein A is derived from acrylic acid and methacrylic acid.
4. The copolymer of claim 1, wherein the monomers of B are selected from the (meth)acrylic acid esters of 1–18 carbon straight, branched or cyclic alcohols and combinations thereof.

5. The copolymer of claim 1, wherein the monomers of B are selected from the group consisting of (meth)acrylic acid esters of 1–12 carbon straight, branched or cyclic alcohols and combinations thereof.

6. The copolymer of claim 1, wherein B is selected from the group consisting of (meth)acrylic acid esters of 1–8 carbon straight, branched or cyclic alcohols and combinations thereof.

7. The copolymer of claim 4, wherein the monomers of B are additionally selected from group consisting of styrene, vinyl esters, vinyl chloride, vinylidene chloride and acryloyl monomers and combinations thereof.

8. The copolymer of claim 4, wherein the monomers of B are additionally selected from the group consisting of (meth) acrylic acid esters of 1–18 carbon straight, branched or cyclic alcohols substituted by one or more of the functionalities selected from the group consisting of hydroxyl, ethers, amides, halides and combinations thereof.

9. The copolymer of claim 1, having a Water Solution Interfacial Tension Value of less than 10 dynes/cm.

10. The copolymer of claim 1, having a Basic Solution Interfacial Tension Value of less than 10 dynes/cm.

11. The polymer of claim 1, wherein the polymer, when added at 2 weight % to a Stock Cosmetic Lotion, increases viscosity no more than 50%.

12. The polymer of claim 1, wherein the polymer, when added at 2 weight % to a Stock Cosmetic Lotion, increases viscosity no more than 25%.

13. The polymer of claim 1, wherein the polymer, when added at 2 weight % to a Stock Cosmetic Lotion, increases viscosity no more than 10%.

14. A composition comprising
a) the copolymer of claim 1, and
b) an organic solvent.

15. The composition of claim 14, wherein the solvent is selected from the group consisting of volatile alkyl silicones, $C_{12-15}$ benzoate esters, C8–18 alkane, and combinations thereof.

16. The composition of claim 14, wherein the solvent is selected from the group consisting of decamethylcyclopentasiloxane and isododecane.

17. A cosmetic composition comprising the polymer of claim 1, said cosmetic composition being selected from the group consisting of hair styling agents, shampoos, dyes, conditioners, rinses, antidandruff preparations, shaving products, hand and body lotions, gels, creams, moisturizers, sunscreen compositions, sunless tanning compositions, cleansers, foundations, toners, astringents, fresheners, masks for the skin; polishes and strengtheners for the nails; underarm deodorants and antiperspirants, bath powders, talcs, bath oils, bubble baths; makeup products for the eyes, cheeks, and lips ; and colognes and perfumes.

18. A cosmetic composition comprising the polymer of claim 1, said cosmetic composition being selected from the group consisting of foundation, mascara, lipstick.

* * * * *

UNITED STATES PATENT AND TRADEMARK OFFICE
CERTIFICATE OF CORRECTION

PATENT NO. : 6,264,934 B1
DATED : July 24, 2001
INVENTOR(S) : Steven S. Kantner, Richard A. Mallo and Ramesh C. Kumar It is certified that error appears in the above-identified patent and that said Letters Patent is hereby corrected as shown below:

<u>Column 1,</u>
Line 40, delete the word "Clariziato" and insert in place thereof -- Clarizia to --.

<u>Column 2,</u>
Line 3, delete the first occurrence of the word "is".

<u>Column 10,</u>
Line 38, delete the word "kilopascals" and insert in place thereof -- kiloPascals --.

<u>Column 14,</u>
Line 14, delete the word "follow" and insert in place thereof -- following --.

<u>Column 16,</u>
Line 11, insert the heading -- Composition Example 7 --.
Line 13, delete "750ºC." and insert in place thereof -- 75ºC. --

Signed and Sealed this

Fifteenth Day of October, 2002

Attest:

Attesting Officer

JAMES E. ROGAN
*Director of the United States Patent and Trademark Office*